United States Patent [19]
Bonadio

[11] Patent Number: 5,803,921
[45] Date of Patent: Sep. 8, 1998

[54] ACCESS PORT DEVICE FOR USE IN SURGERY

[75] Inventor: Frank Bonadio, County Wicklow, Ireland

[73] Assignee: Gaya Limited, Dublin, Ireland

[21] Appl. No.: 433,498

[22] PCT Filed: Feb. 20, 1995

[86] PCT No.: PCT/IE95/00020

§ 371 Date: May 8, 1995

§ 102(e) Date: May 8, 1995

[87] PCT Pub. No.: WO95/22289

PCT Pub. Date: Aug. 24, 1995

[30] Foreign Application Priority Data

| Feb. 18, 1994 | [IE] | Ireland | S940150 |
| Aug. 5, 1994 | [IE] | Ireland | S940613 |
| Dec. 7, 1994 | [IE] | Ireland | S940960 |
| Jan. 25, 1995 | [IE] | Ireland | S950055 |

[51] Int. Cl.$^6$ ................................................ A61M 29/00
[52] U.S. Cl. .............................. 606/1; 606/108; 606/185; 604/162; 604/169; 604/174; 604/180
[58] Field of Search ................................. 626/1, 108, 185, 626/213; 604/167, 169, 174, 180; 18/850, 853, 584, 856

[56] References Cited

U.S. PATENT DOCUMENTS

| 2,219,564 | 10/1940 | Reyniers . |
| 2,695,608 | 11/1954 | Gibbon . |
| 2,835,253 | 5/1958 | Borgeson . |
| 5,234,455 | 8/1993 | Mulhollan . |
| 5,366,478 | 11/1994 | Brinkerhoff et al. ................ 606/213 |
| 5,391,156 | 2/1995 | Hildwein et al. .................. 606/213 |
| 5,437,683 | 8/1995 | Neumann et al. .................. 606/213 |
| 5,480,410 | 1/1996 | Cushieri et al. .................. 606/213 |
| 5,511,564 | 4/1996 | Wilk ................................ 606/1 |
| 5,514,133 | 5/1996 | Golub et al. ...................... 626/1 |

FOREIGN PATENT DOCUMENTS

| 0537768 | 4/1993 | European Pat. Off. . |
| WO8606272 | 11/1986 | WIPO . |
| WO9305740 | 4/1993 | WIPO . |
| WO9507056 | 3/1995 | WIPO . |

*Primary Examiner*—Michael Buiz
*Assistant Examiner*—Daphna Shai
*Attorney, Agent, or Firm*—Sixbey, Friedman, Leedom & Ferguson PC; Daniel W. Sixbey

[57] ABSTRACT

An access port device (40) for use in surgery is provided which comprises a sleeve (41,42) having an exit opening located at a distal end thereof for insertion into an incision made in a patient's body, the exit opening allowing access to the patient's body cavity. The device (40) also includes exit opening sealing means for insertion into the incision. There is an entry opening located at a proximal end of the sleeve (41,42) and entry sealing means for sealing the device in the region of the entry opening, so that when the patient's body cavity is inflated by gas, the exit sealing means and the entry sealing means prevent substantial leakage of gas from the patient's body cavity while the entry sealing means also provides access for a surgeon's hand or surgical instrument and sealing about the arm remaining outside the access port device. The invention also relates to surgical instruments for use with such an access port and to a surgical drape for use in surgery using the access port and instruments of the invention.

43 Claims, 12 Drawing Sheets

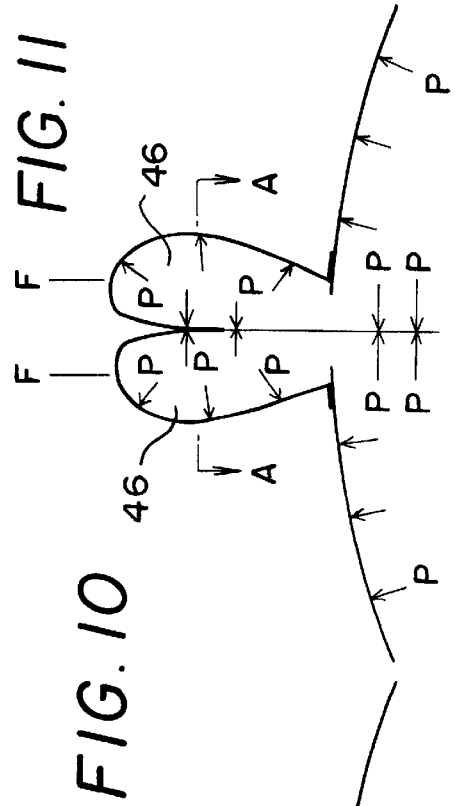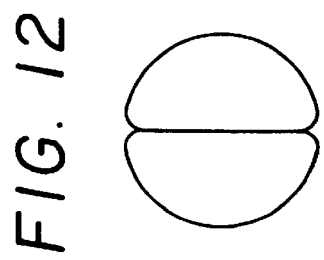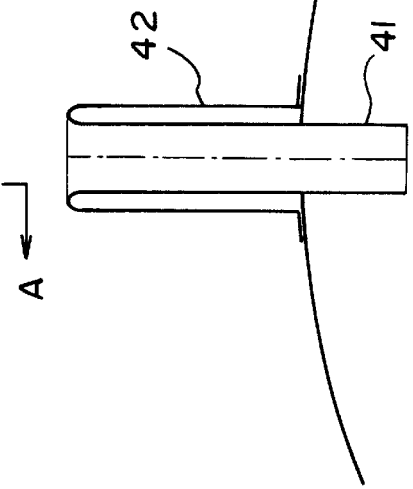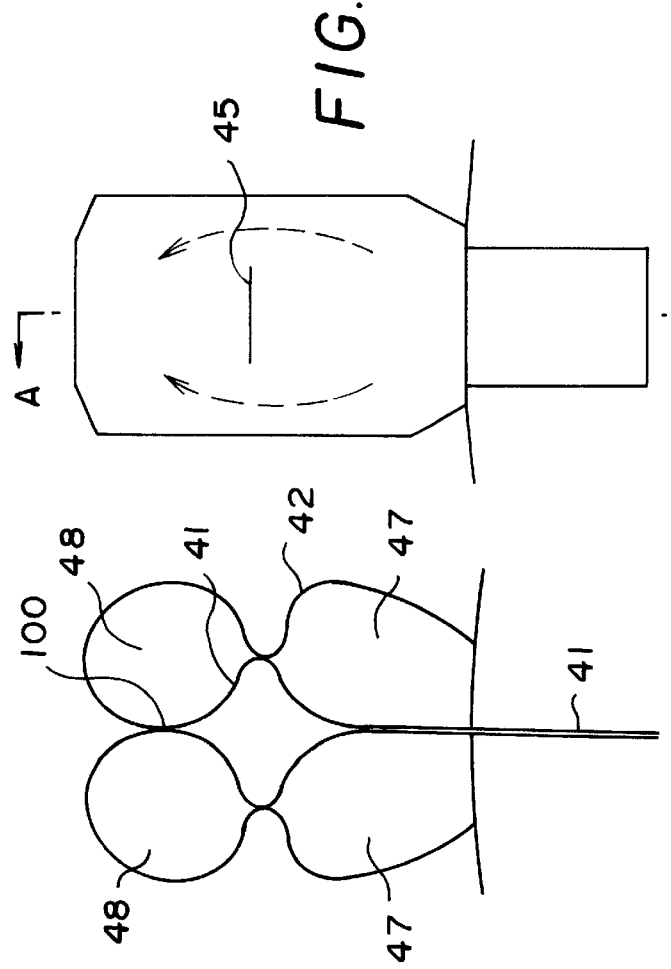

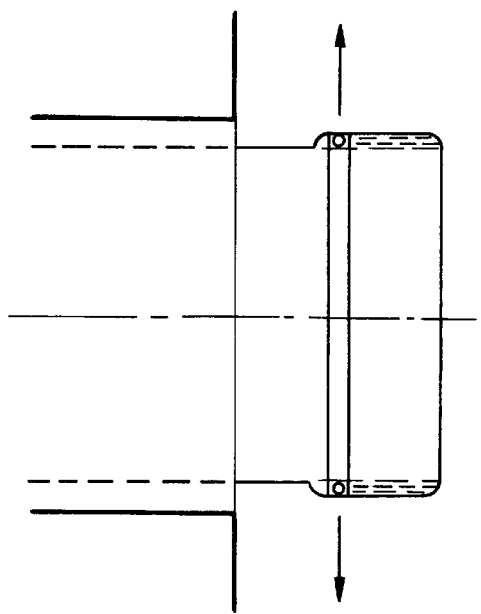
FIG. 26
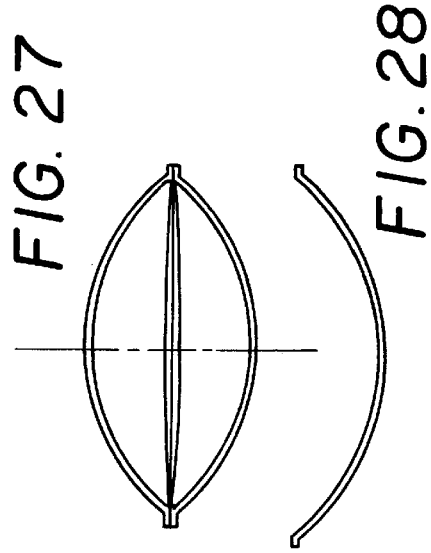
FIG. 27
FIG. 28
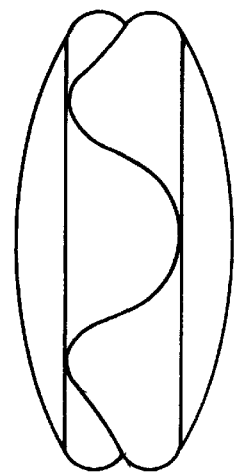
FIG. 19
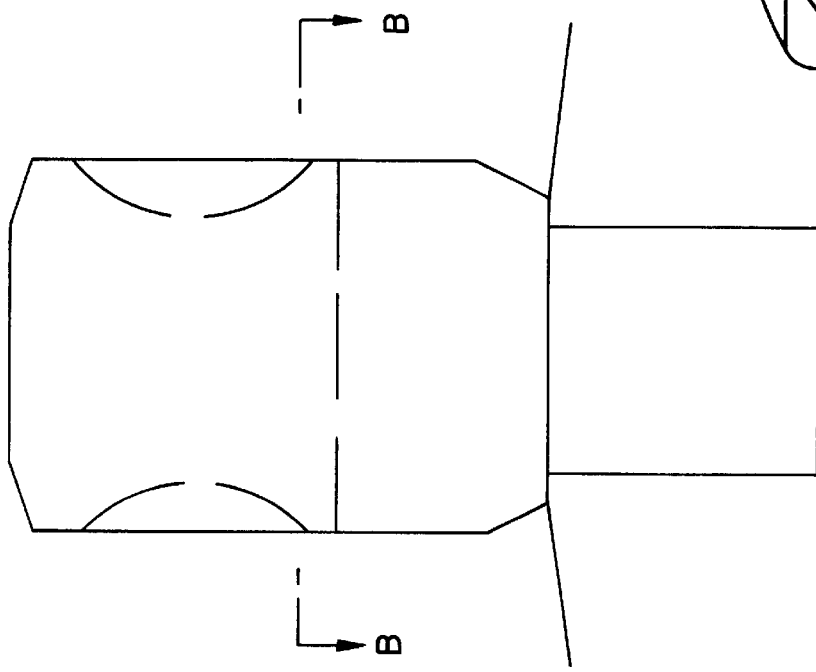
FIG. 18

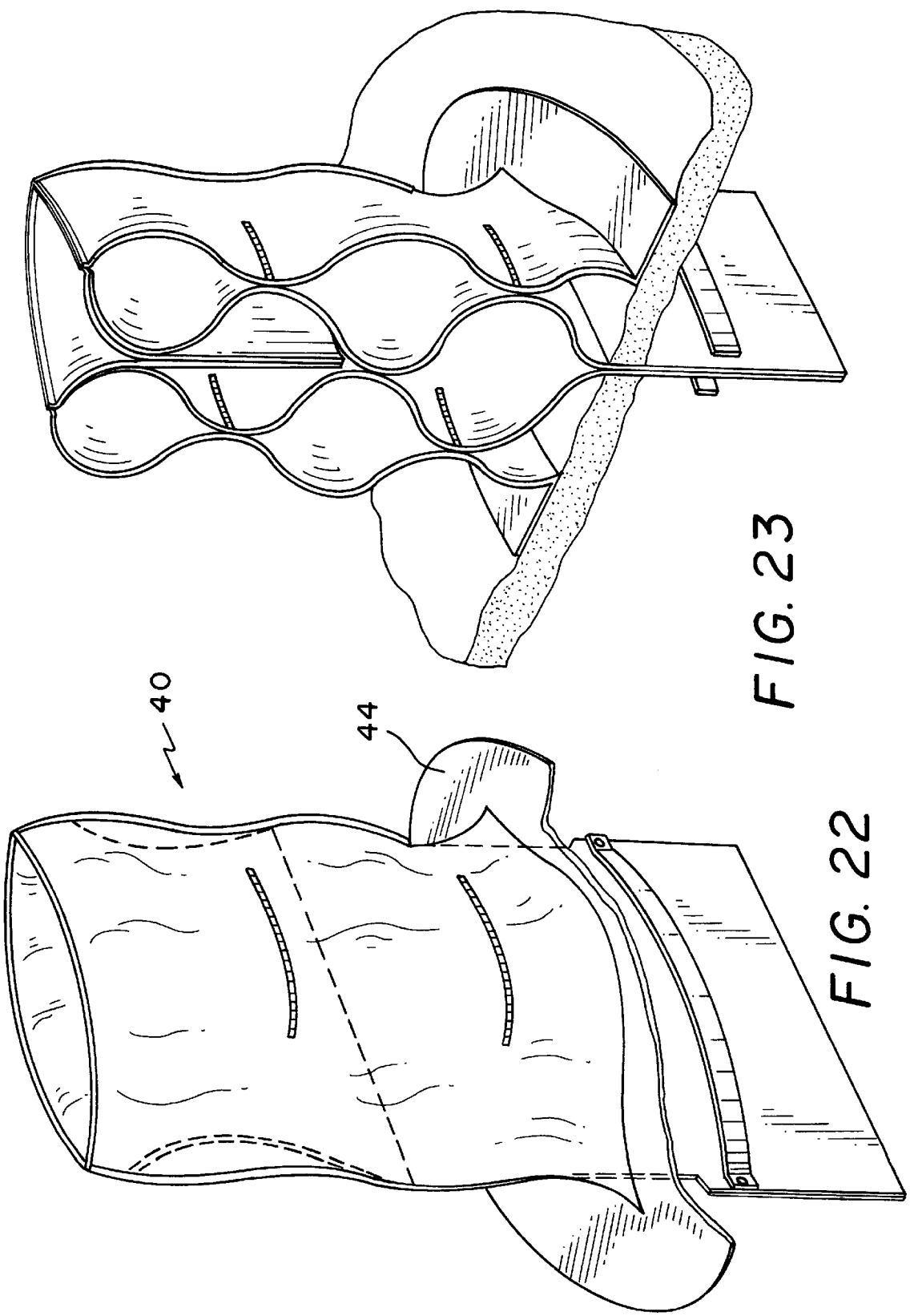

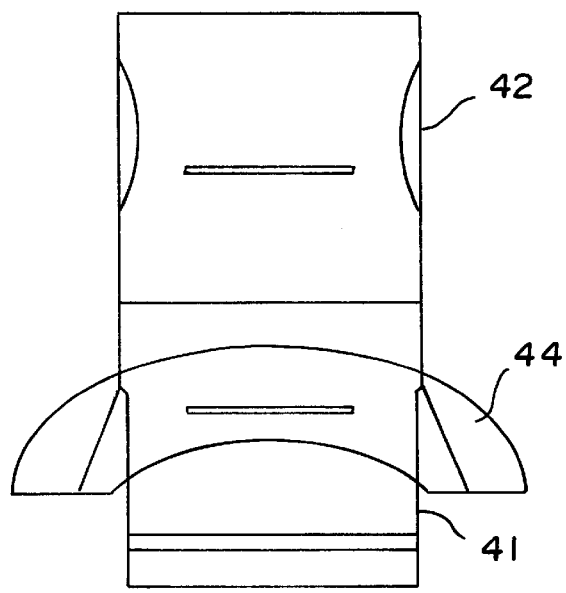
FIG. 24
FIG. 25
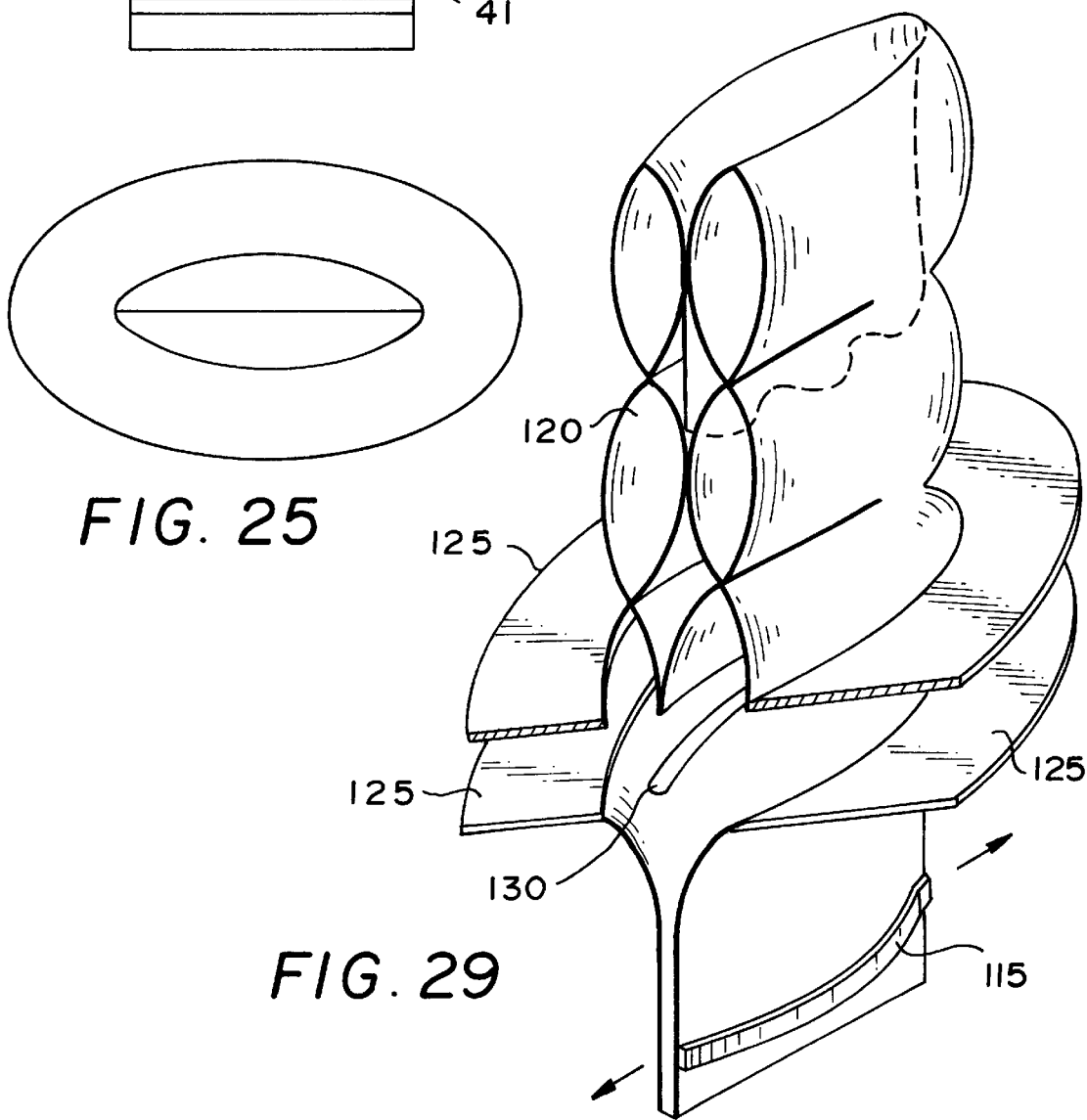
FIG. 29

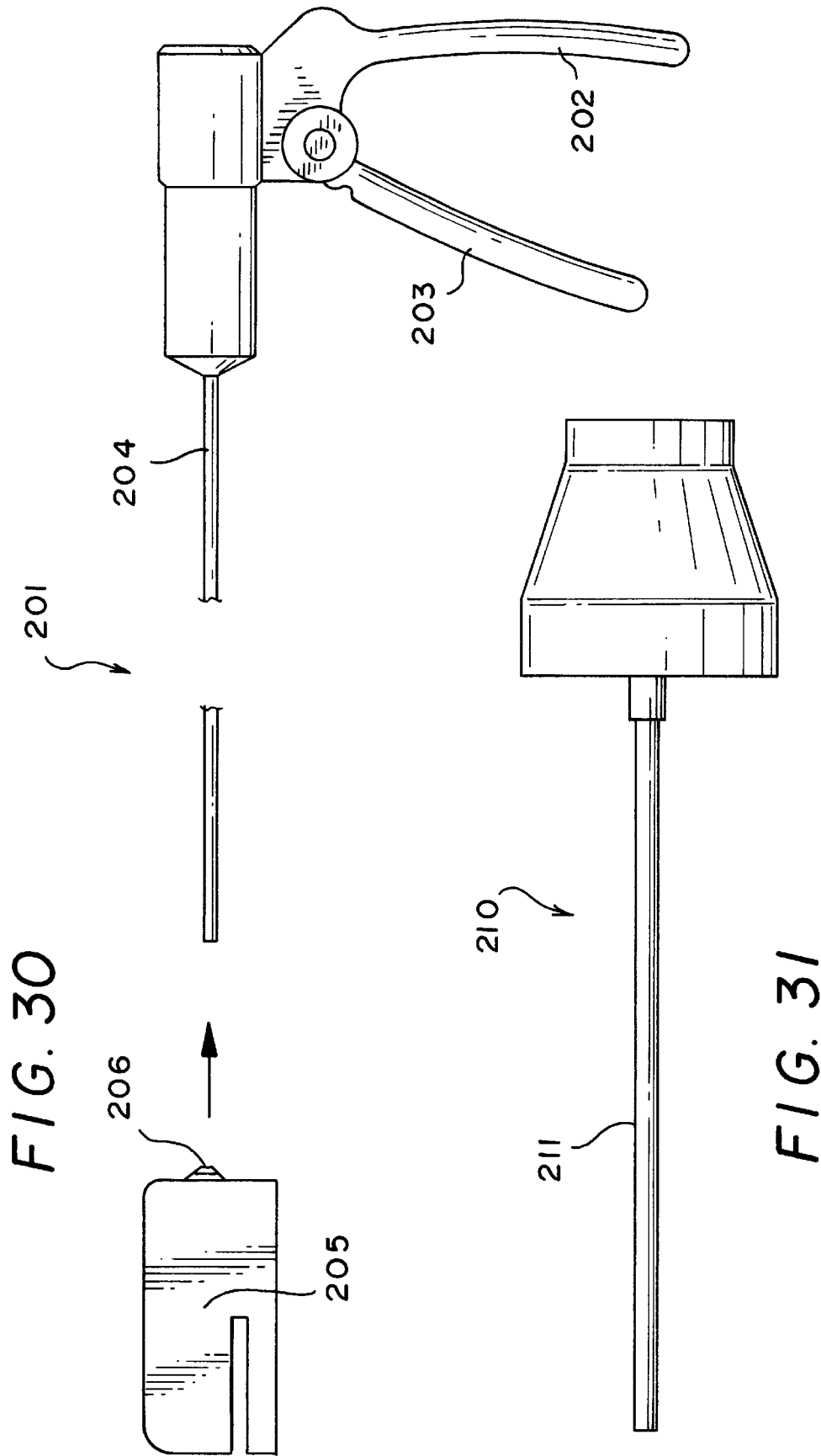

ACCESS PORT DEVICE FOR USE IN SURGERY

The present invention relates to surgical apparatus, including an access port for minimally invasive surgery, surgical instruments for use with such a port and a surgical drape for use in surgery using the access port and instruments of the invention.

Minimally invasive surgery is surgery carried out by causing the minimum amount of trauma by incision in a patient's body. The apparatus of the present invention enables laproscopic hand/instrument assisted surgery to be performed and should substantially increase the number and variety of surgical procedures which can be performed without requiring open surgery. Minimally invasive surgery almost invariably involves deliberately introducing gas into a patient's peritoneal cavity to cause pneumoperitoneum.

A sleeve for use in minimally invasive surgery forms the subject matter of a co-pending unpublished PCT Patent Application No. PCT/IE94/00045 entitled "Apparatus for use in surgery". The purpose of this prior art sleeve is to create a controlled pressurized environment within the sleeve while allowing a surgeon's arm to pass through the sleeve. For surgery, gas is pumped into the patient's body cavity where the surgery is to be performed and the purpose of the sleeve is to prevent gas escaping from the patient's body cavity while allowing the surgeon to operate using minimally invasive surgery techniques. The patent application proposes a sleeve having a flange at its distal end provided with adhesive for adhering the device to the patient's body or alternatively having a mounting ring at its distal end surrounding the incision in a patient's body.

However, the prior art device suffers from the disadvantage, inter alia, that in use, the sleeve protrudes upwardly from the patient and may interfere with the activities of the surgery team.

The prior art device also suffers from the disadvantage that the sleeve includes a sealing means to seal the sleeve against the surgeon's upper forearm, which sealing means the surgeon has to effect himself by clamping the device to his arm. The clamp must be quite tight to avoid gas leak around the area of the seal.

A further problem associated with the use of sleeves of the kind described in co-pending patent application no. PCT/IE94/00045, is that a phenomenon known as "tenting" may occur. "Tenting" means that when the sleeve is adhered the patient's skin or to sterilised wrapping material (also known and referred herein as "surgical drape" or "incise drape") which may in turn be adhered to the patient, the sleeve may have a tendency to pull away from the patient and "lift" the skin upwardly from the patient's abdomen which is inflated using gas for surgery. The sterilised wrapping material referred to above is also known as "surgical drape" or "incise drape". These latter terms will be used in the following description.

When surgery is being performed, the surgeon generally relies on a trocar and trocar sleeve to give access to the abdominal cavity while maintaining pneumoperitoneum. The trocar must be sharp to cut through and separate the muscle and facia surrounding the abdominal cavity. The trocar sleeve allows entry and exit of instruments therethrough while sealing the pneumoperitoneum. A valve is included at the entry of the trocar sleeve which opens to allow a surgical instrument such as a dissecting scissors, a stapling instrument, forceps and such like to pass through the valve and be moved through the trocar sleeve into the abdominal cavity where the instruments are manipulated by the surgeon. The valve closes when the instrument is withdrawn.

Clearly, the dimensions of the surgical instruments must be sized so that those instruments can fit through the trocar sleeve.

Known devices suffer from the disadvantage that when the surgeon wishes to use a different instrument which is larger than the internal diameter of the trocar, he must make an incision in the patient to gain access to the tissue or organ or remove the tissue or portion of say the bowel through the incision to work on it. Such an incision will lose the pneumoperitoneum.

A surgical incise drape is a thin film polymeric material usually made from polyethylene. It is transparent with a mild adhesive on one side and a smooth non-adhesive opposing side. The adhesive side is placed onto the patient, over the entire abdomen or thorax, with careful attention not to create any air pockets that could propagate failure of the device to adhere. These drapes are intended to isolate transmission of micro-organisms on the surface of the patient's skin during surgery into the incision wound. The surgeon is able to make an incision through the drape without disrupting the adhesion of the drape to the skin even in the area immediately adjacent to incision.

The adhesive properties of the incise drape are well known to have a low peel strength (if one was to peel from the edge of the device), and very high pull strength (if one could find attachment within the periphery of the drape. This action is largely due to the elastic properties of the drape and the large surface area that it covers over the patients skin.

Regularly, it is required to anchor a component to the incise drape. In the prior art this anchoring is achieved by double sided strong adhesive tape connected to a polymer flange.

The present invention seeks to alleviate the disadvantages associated with prior art surgical apparatus.

In a first aspect, the present invention accordingly provides an access port device for use in surgery comprising a sleeve having an exit opening located at a distal end thereof for insertion into an incision made in a patient's body, the exit opening allowing access to the patient's body cavity, the device further including exit opening sealing means for insertion into the incision, whereby when the patient's body cavity is inflated by gas, the exit sealing means prevents substantial leakage of gas from the patient's body cavity while providing access for a surgeon's hand or surgical instrument.

An entry opening is located at a proximal end of the sleeve and entry sealing means are provided for sealing the device in the region of the entry opening, whereby when the patient's body cavity is inflated by gas, the entry sealing means assists in preventing substantial leakage of gas from the patient's body cavity while providing access for a surgeon's hand and sealing about the arm remaining outside the access port device.

The entry sealing means may comprise an inflatable chamber provided on the proximal end of the sleeve. The inflation chamber may be inflated using a separate valve from that used to inflate the patient's body cavity. When the access port is in use, fluid communication is possible between the inflated chamber and the patient's body cavity so as to equalise the pressure in the inflated chamber and in the body cavity.

The sleeve may be provided with a flange having adhesive thereon for affixing the access port externally to the patient. The flange may be located between the proximal and distal ends of the sleeve so that in use, when the flange is adhered to the patient's body, the distal end of the sleeve is inserted through the incision and is inside the patient's body cavity and the access port projects a short distance above the patient's body.

When the distal end of the sleeve is inserted through the incision, the patient's muscle tissue around the incision may act as a sealing means for assisting in sealing the intermediate portion of the sleeve between the distal end and the proximal end.

The entry sealing means may comprise an inflatable chamber arranged in surrounding relation to the sleeve and capable of exerting a pressure on the sleeve causing at least a portion of it to collapse thereby sealing the entry opening.

The inflatable chamber may not be in fluid communication with the sleeve, so that in use, the chamber is not in fluid communication with the patient's body cavity and thus the pressure inside the inflatable chamber may be different from the pressure inside the patient's body cavity.

Alternatively, the inflatable chamber may be in fluid communication with the sleeve.

The inflatable chamber is of generally "hour-glass" profile defining an upper chamber and a lower chamber, the lower chamber being insertable into the incision made in the patient's body cavity.

The sleeve and inflatable chamber may be co-axial and include sheets of a gas permeable flexible material bonded at their common proximal end and side edges, with the sleeve being within the inflatable chamber in the proximal region. The chamber may be defined between an outer sleeve located about the inner sleeve in the proximal region of the device and located within the inner sleeve and extending from the proximal end toward the distal end is a flap valve formed between two further sheets of flexible material.

The distal edges of the flap valve may be of a feathered construction and the sheets and edges of the flap valve are collapsible towards each other to form a seal when the chamber is pressurised.

The flap valve may be connected to the inner and outer sleeves at two locations along each side thereof whereby the region of the flap valve between the two locations can conform about a portion of the surgeon's hand or arm.

The inner and outer sleeves may be connected together by joins at specific locations so as to divide the inflatable chamber into upper and lower sub-chambers in fluid communication so that when pressurised, the sub-chambers define at least one contiguous seal of surfaces forming the entry sealing means or a part thereof. The joins may comprise a plurality of opposed welds.

The exit sealing means is provided by the sheets of the sleeve being collapsible by gas pressure within the abdominal cavity of the patient at or adjacent, the distal edges of the sleeve.

A separate tensioning device may be provided in the distal region of the sleeve spaced from the distal edge to place the sheets under a generally transverse tension thereby creating a taut region across the sleeve operable as a further seal as part of the exit sealing means.

The tensioning device may comprise a pair of opposed arcuate bands operable to prevent retraction of the sleeve from the abdominal cavity. Wings may be provided at the side edges of the sleeve to provide anchoring points for the opposed arcuate bands.

In a second aspect of the present invention, there is provided a surgical instrument comprising an elongate shaft, the dimensions of which are appropriately sized so as to enable the shaft to be inserted and retracted through a trocar sleeve, a detachable instrumentation head and means for detachably connecting the instrumentation head to the shaft whereby the shaft can be moved through the trocar sleeve without the instrumentation head being connected thereto and the instrumentation head can be detachably connected to the shaft within abdominal cavity of a patient.

Advantageously, the detachable head does not need to be of a size necessary to enable it to pass through the trocar sleeve. The detachable instrumentation head can be carried into the abdominal cavity in the surgeon's hand. This is envisaged both in the situation where the surgery is being carried out by minimally invasive surgery and where surgery is by open surgery. In the case of minimally invasive surgery, access ports are described in the first aspect of the present invention which enable a surgeon's hand to enter the abdominal cavity for surgery. The detachable instrumentation head can be carried into the abdominal cavity in the surgeon's hand.

In use, the surgeon can attach the instrumentation head to the shaft inside the abdominal cavity. This has the advantage that the instrument does not have to be withdrawn from the abdominal cavity via the trocar sleeve and a different instrument inserted.

In a third aspect, of the present invention, there is provided a surgical device having at least one surface provided with a strong adhesive adapted to be used in combination with a surgical incise drape having a low peel strength adhesive, in use the device being secured by the strong adhesive to a non-adhesive side of the drape.

Conveniently, the strong adhesive is applied to an area of the surgical device. Alternatively, the strong adhesive is provided on a site on the non-adhesive side of the incise drape.

Direct attachment of a strong adhesive to a patient is not desirable. If strong adhesives are used directly on a patient, it can cause damage to the patient's skin. They would be difficult to remove, and may cause negative reaction to the skin. The use of the incise drape will cause a barrier between the patient and the strong adhesive, at the same time allow a strong pull force at the attachment site of the drape.

The invention will now be described more particularly with reference to the accompanying drawings, which show, by way of example only, various embodiments of surgical apparatus in accordance with the invention.

FIG. 10 is a schematic diagram of the access port of the invention without any transverse weld lines with the port shown in use, inserted in an incision site in a patient;

FIG. 11 is a schematic sectional elevation showing the access port in its inflated state;

FIG. 12 is a sectional view along line A-A of FIG. 11;

FIG. 13 is a schematic diagram of the access port of the invention showing the inclusion of a single weld line;

FIG. 14 is a sectional view along the line A—A of FIG. 13;

FIGS. 17, 18 and 19 are schematic diagrams of the access port of the invention showing the inclusion of a flap valve;

FIG. 22 is a perspective view of a third embodiment of the device;

FIG. 23 is a sectional view of FIG. 22;

FIG. 24 is a plan view of the third embodiment;

FIG. 25 is a plan view of the third embodiment showing the device from the distal end;

FIG. 26 is a more detailed view of the distal end of the third and fourth embodiments;

FIG. 27 is a plan view of the tensioning device;

FIG. 28 is a plan view of one side of the tensioning device;

FIG. 29 is a sectional view of a further embodiment of the access port;

FIG. 30 is a side view of the surgical instrument with the detachable instrumentation head shown in a detached position in which it is separated from the shaft of the surgical instrument; and FIG. 31 is a side view of a trocar sleeve.

Figure 1:
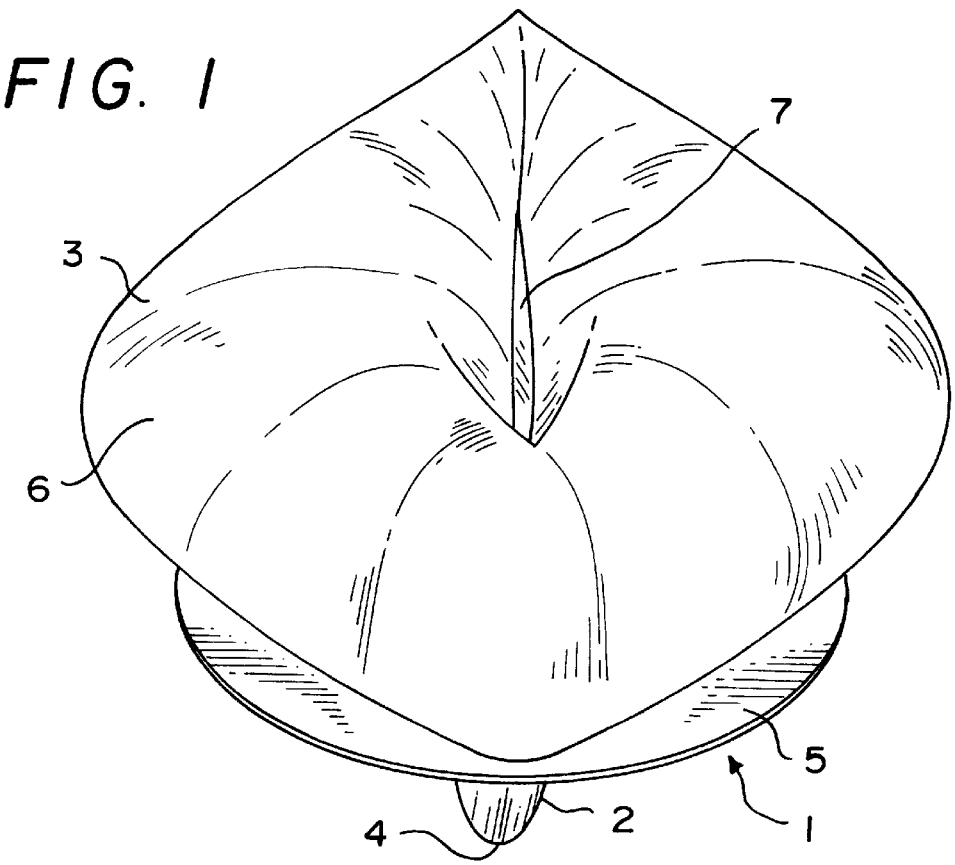
FIG. 1 is a perspective view, of a first embodiment of the access port device of the present invention, from above showing the proximal end of the device uppermost.
Figure 2:
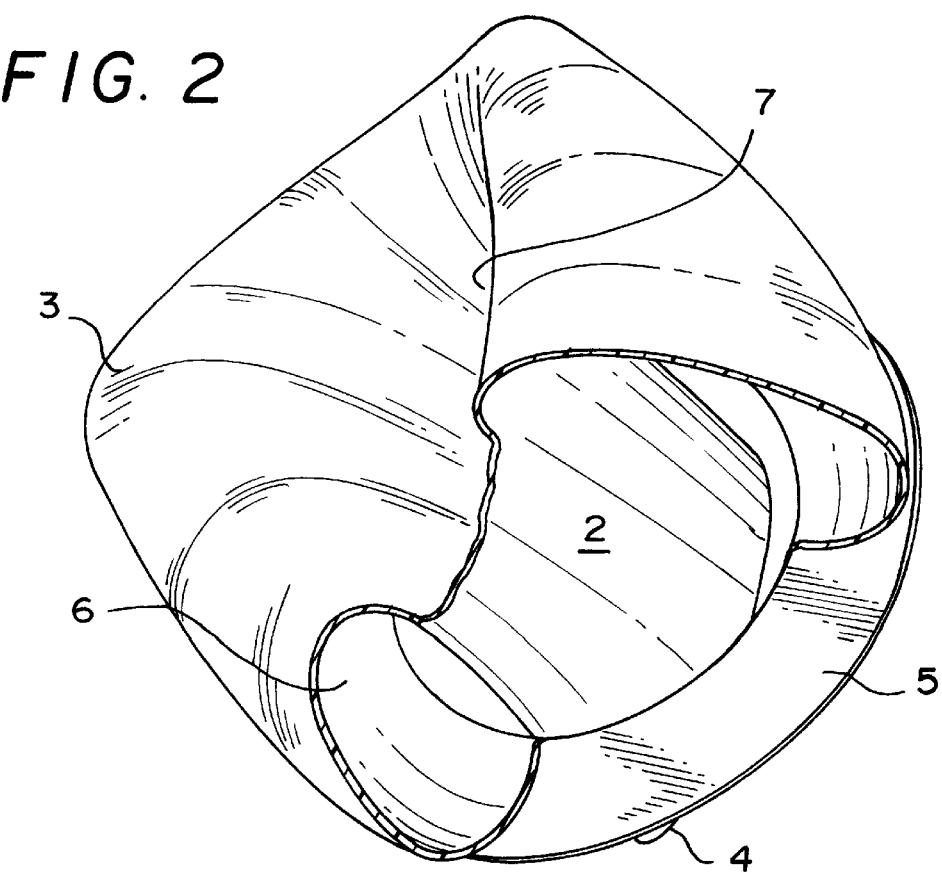
FIG. 2 is also a perspective view of the first embodiment from above, with a portion removed, for clarity.
Figure 3:
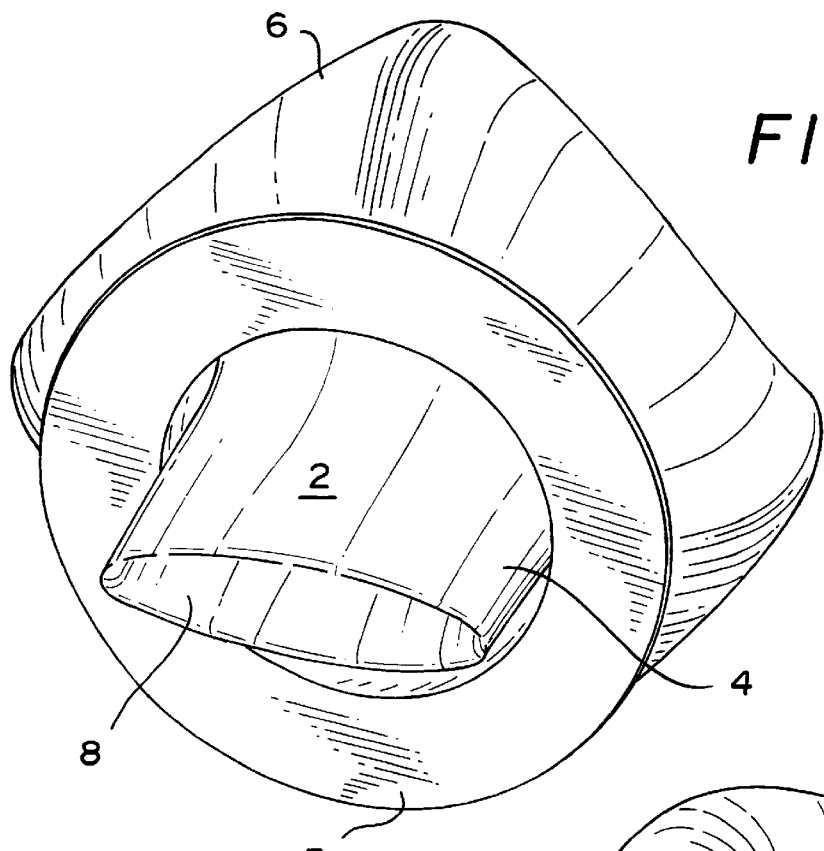
FIG. 3 is a perspective view of the first embodiment from underneath.
Figure 4:
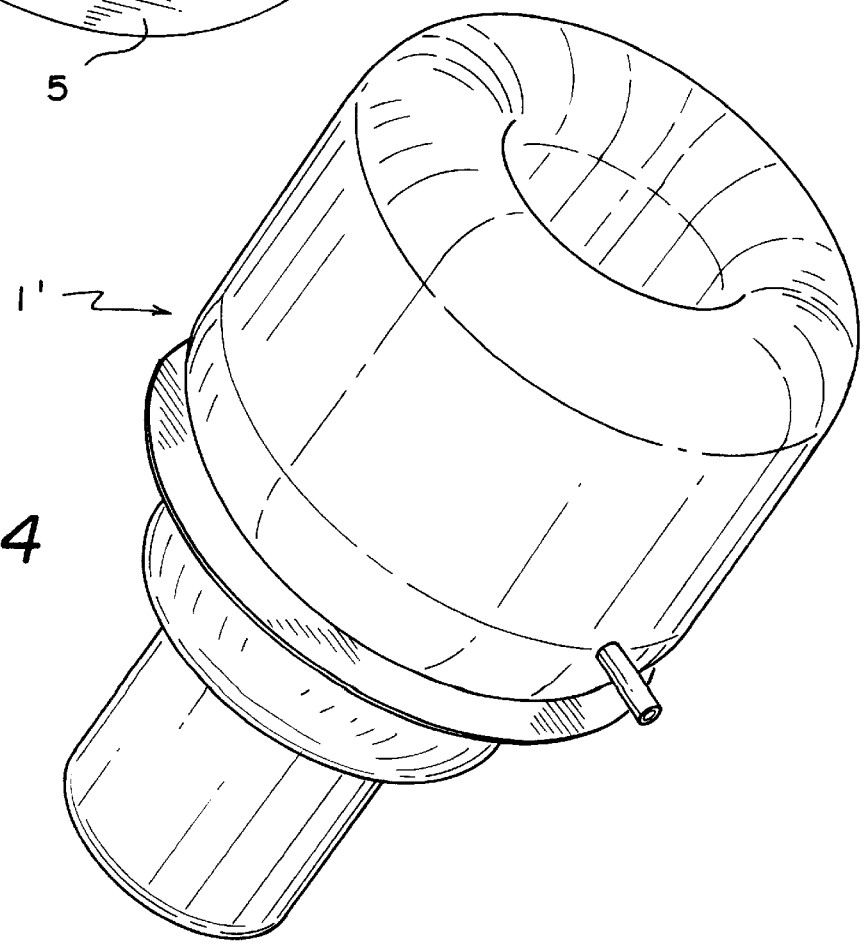
FIG. 4 is a perspective view of a second embodiment of the access port of the present invention.
Figure 5:
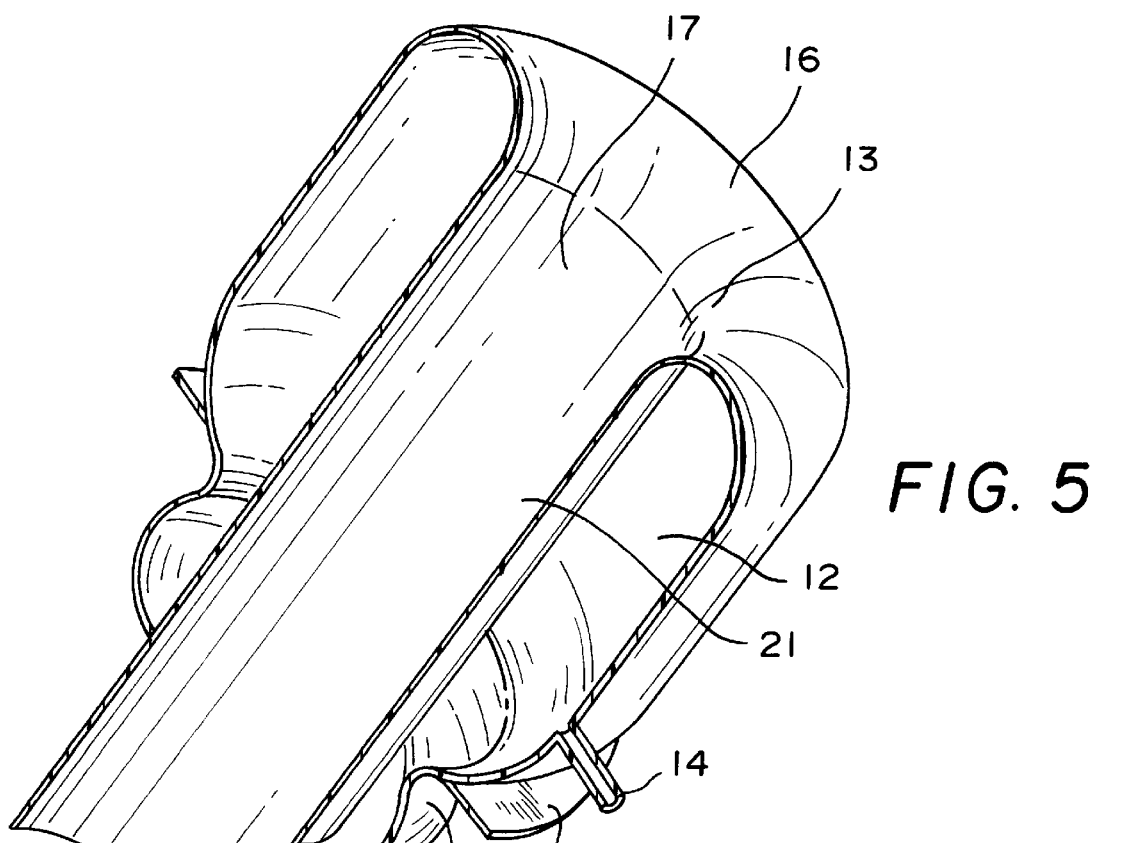
FIG. 5 is a perspective cut-away sectional view of the the second embodiment.

Referring to the FIGS. 1, 2 and 3 of the drawings, the first embodiment of the access port is indicated generally by reference numeral 1 and comprises a sleeve 2 having a proximal end 3 and a distal end 4. The proximal end 3 of the sleeve 2 comprises a flange 5 and an inflatable chamber 6 having a entry opening (mouth) 7 through which a surgeon's hand may enter.

For surgery, an incision is made in the body of the patient, such an incision being made preferably along the muscle rather than across the muscle of the patient.

In order to assist in securely affixing the access port 1 to the patient's body, an adhesive sterile wrapping material may be adhered to the patient's body and an incision can made through the wrapping material. The distal end 4 of the sleeve 2 is inserted into the incision and is pushed into the body cavity of the patient (which is not inflated at this stage) until the flange 5 contacts the wrapping material or the patient's skin, as the case may be if adhesive wrapping material is not used. The adhesive flange 5 is then adhered to the wrapping material or the skin as the case may be, thereby securely affixing the access port 1 to the patient. The action of the muscle tissue around the incision causes the muscle tissue to press against the sleeve 2.

In order to seal the entry opening 7, gas is pumped into the inflatable chamber 6 causing it to inflate and thereby seal the entry opening 7. The patient's body cavity is then inflated. The gas used to inflate the inflatable chamber 7 may be pumped into the chamber 7 via a different valve from that used to inflate the patient's body cavity.

Since fluid communication between the inflated chamber 6 and the patient's body cavity is possible when the access port 1 is in use, the pressure within the inflated chamber 6 is the same as the pressure within the patient's body cavity.

The portion of the sleeve 2 which in use, is located within the inflated abdominal cavity of the patient is also subjected to an inwardly-directed pressure due to the pressure existing in the patient's abdominal cavity and that portion of the sleeve collapses to form a seal.

When the surgeon desires to insert his gloved hand through the access port, he pushes his gloved hand through the entry opening 7 and down through the sleeve 2. As a surgeon forces his arm through the entry opening 7, the now inflated chamber 6 seals against his forearm. Since the seal is formed about a larger surface area on the surgeon's forearm than is the case in the prior art, the blood supply to the surgeon's finger tips does not become restricted. The surgeon pushes his gloved hand through the incision made in the patient and the action of the muscle tissue at the incision site has the effect of gripping the sleeve 2 and sealing it against the surgeon's forearm. Therefore, there are two seals in operation, namely, one seal which forms around the surgeon's forearm due to the action of muscle tissue at the incision site pressing and sealing the sleeve 2 against the surgeon's forearm and a second seal at the entry opening 7 of the access port 1 where the inflated chamber 6 seals about and against the surgeon's upper forearm.

As the surgeon withdraws his hand out of the access port 1 of the invention, the muscle tissue around the incision site clamps in on the sleeve 2 creating a seal against the sleeve 2 and as the surgeon withdraws his hand from the entry opening 7, the seal is maintained.

A further advantage of the access port 1 of the present invention is that manipulation of the access port can be carried out using one hand. The prior art device requires two hands in order for the surgeon to remove his "operating" hand out of the sleeve. Furthermore, because the distal end 4 of the sleeve 2 is inside the patient's body cavity, as the surgeon retracts his gloved hand, if his glove rubs against the side of the sleeve 2, the incision site does not come into contact with any infected tissue which might be carried upwardly from the operation site on the surgeon's hand or instrument.

It will be understood that the size of the access port can be varied to accommodate, for instance only one finger rather than the entire hand and arm of the surgeon and also may accommodate instruments. It is envisaged that it will be possible for the surgeon to take an instrument down through the sleeve while carrying the instrument in his hand.

The access port device may be manufactured from any flexible, gas impermeable, sterilisable, biocompatible material, for instance polyethylene.

Referring now to FIGS. 4 to 7, the access device in a second embodiment of the invention is indicated generally by the reference numeral 1' and comprises an inflatable chamber having an upper portion 12 and a lower portion 13 which are in fluid communication with each other and having an inlet pipe 14 for supplying gas to inflate both the upper portion 12 and lower portion 13 of the inflatable chamber. A separate pipe is used to inflate the patient's abdominal cavity. The device 1' also includes an adhesive flange 15 which can be adhered to the patient's skin or to the wrapping material, if such is used. The upper portion 12 of the chamber includes a lip 16 defining an entry opening 17 at the proximal end 18 of sleeve 21, leading to an exit opening 19 at the distal end 20 of the sleeve 21. The device 1' therefore has the advantage that the pressure in the inflated chamber can be controlled independently from the pressure in the patient's abdominal cavity and therefore there can be a pressure differential between the pressure in the cavity and the pressure in the chamber of the access device 1'.

In order to use the device 1', the surgeon pushes his gloved hand through the entry opening 17 of the device 1' and down through the sleeve 21. For surgery, an incision is made in the body of the patient, such an incision preferably, being made along the muscle rather than across the muscle of the patient. The distal end 20 of the sleeve 21 together with the lower portion 13 of the inflatable chamber are inserted into the body cavity of the patient (which is not yet inflated, at this stage) until the flange 15 contacts the patient's skin or to the wrapping securing means so as to securely hold the access device 1' in place on the patient's body.

To use the device 1', gas is pumped into the inflatable, chamber via pipe 14 until both the upper portion 12 and the lower portion 13 are fully inflated. The action of the muscle tissue around the incision causes the muscle tissue to press against the indented zone 22 defined between the now inflated portion 12 and inflated lower portion 13 of the chamber.

The patient's body cavity is then inflated. Since fluid communication is not possible between the patient's body cavity and the inflated chamber of device 1', the pressure within the inflated chamber 6 is not necessarily the same as the pressure within the patient's body cavity.

Figure 6:
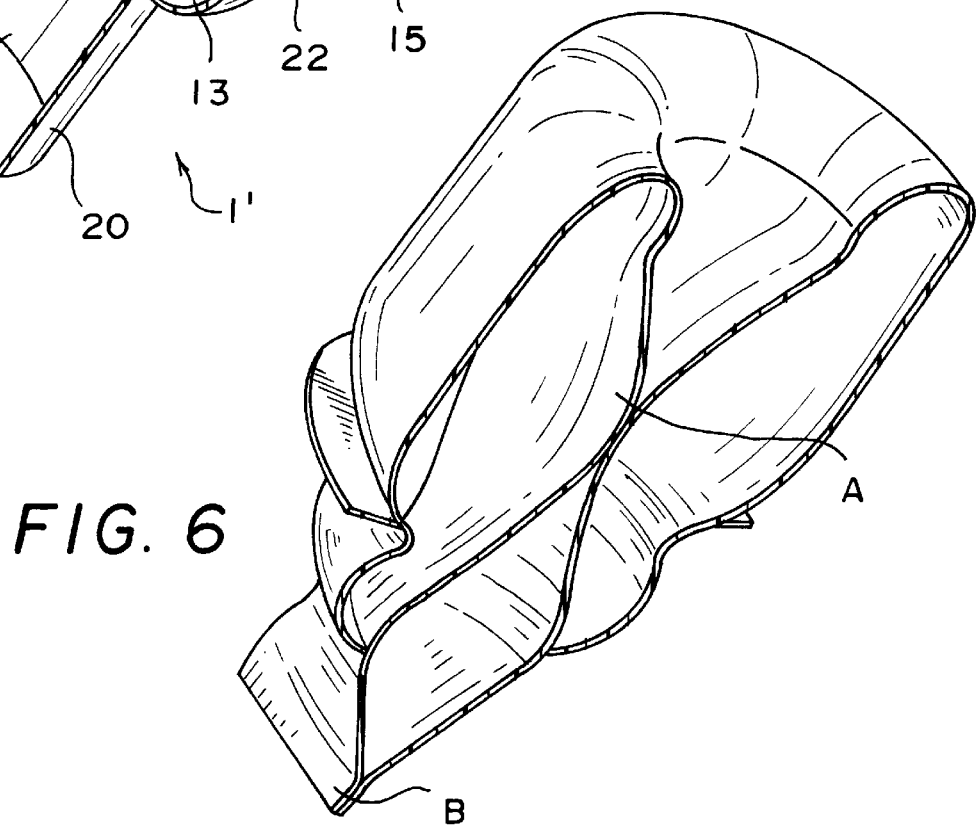
FIG. 6 is another perspective cut-away sectional view of the second embodiment.
Figure 7:
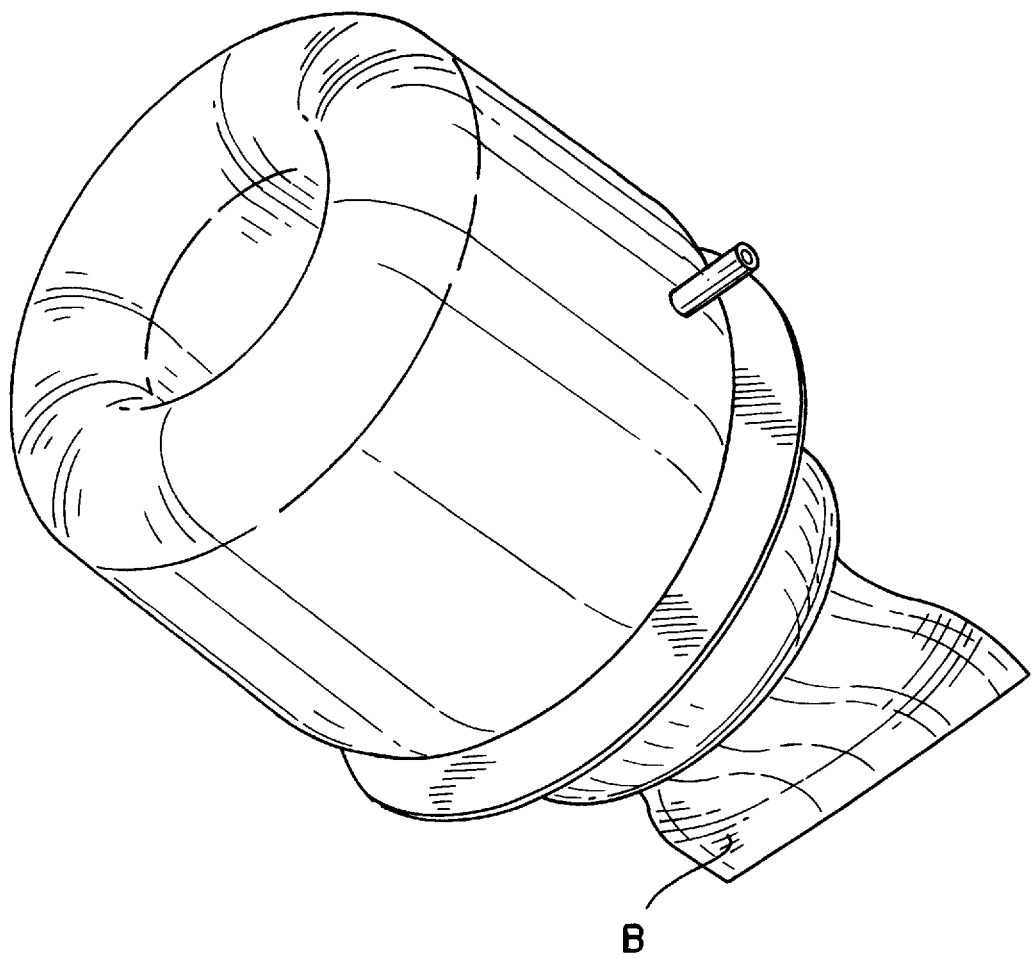
FIG. 7 is another perspective view of the second embodiment.

The pressure in the chamber exerts an inward pressure on the sleeve and as shown in FIG. 6 the sleeve 21 along the area indicated by the letter A. Similarly, the portion of the sleeve 21 which is in use, located within the inflated abdominal cavity of the patient is also subjected to an inwardly-directed pressure due to the pressure existing in the patient's abdominal cavity and that portion of the sleeve also collapses as indicated by reference numeral B on FIGS. 6 and 7 thus creating a seal at a distal end of the device.

The areas A and B respectively act as seals to prevent gas leakage from the patient. Furthermore, they bear against the upper arm and lower arm respectively, of a surgeon, when the surgeon's hand is inserted through the sleeve and into the patient's abdominal cavity.

Figure 9:
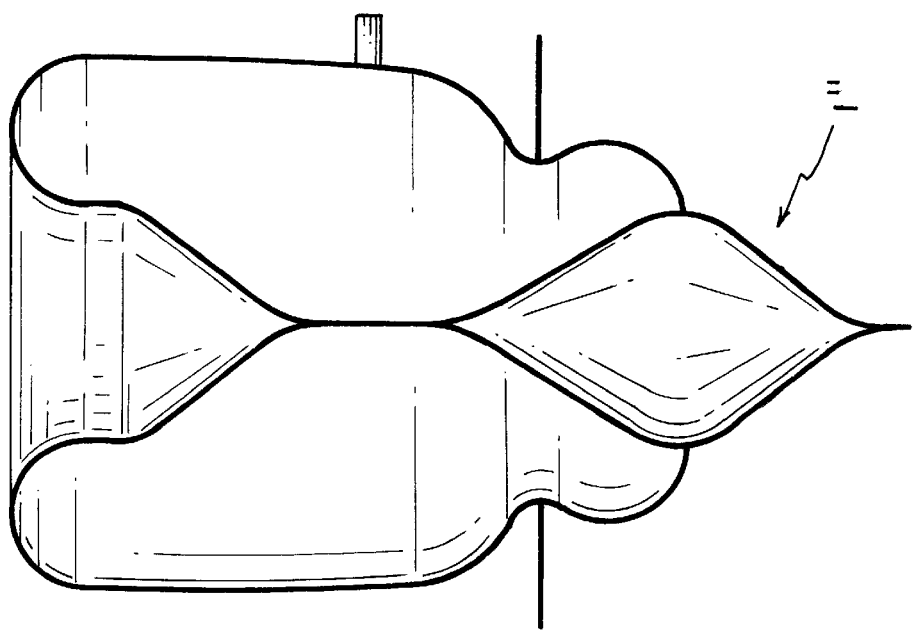
FIG. 9 is a cross-sectional view of the second embodiment at right angles to the cross-sectional view of FIG. 8.
Figure 8:
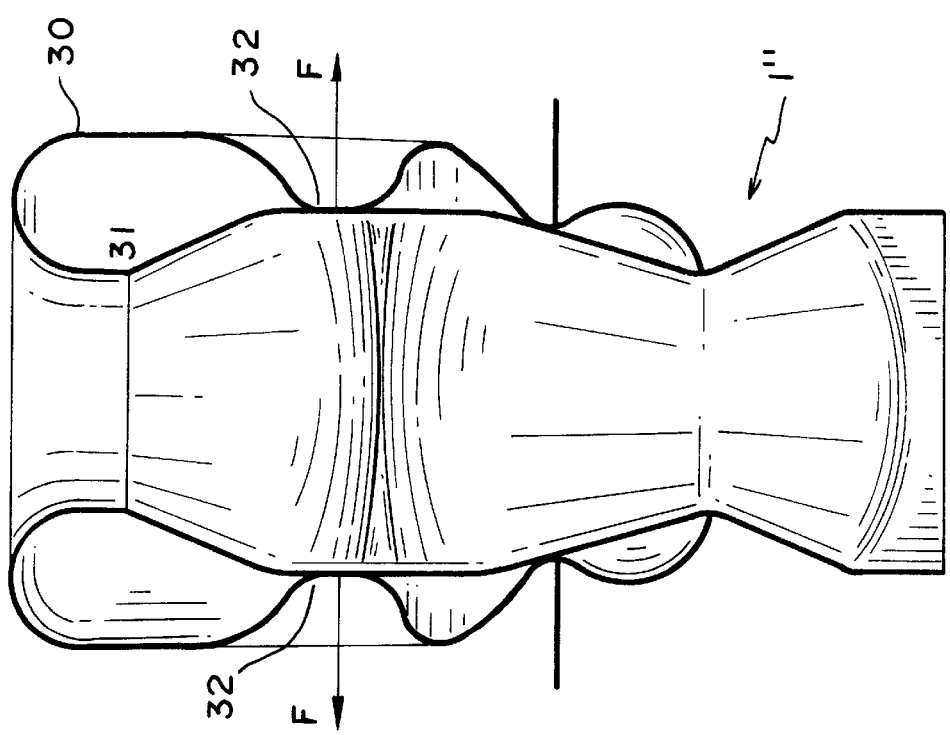
FIG. 8 is a cross-sectional view of the second embodiment.
Figure 17:
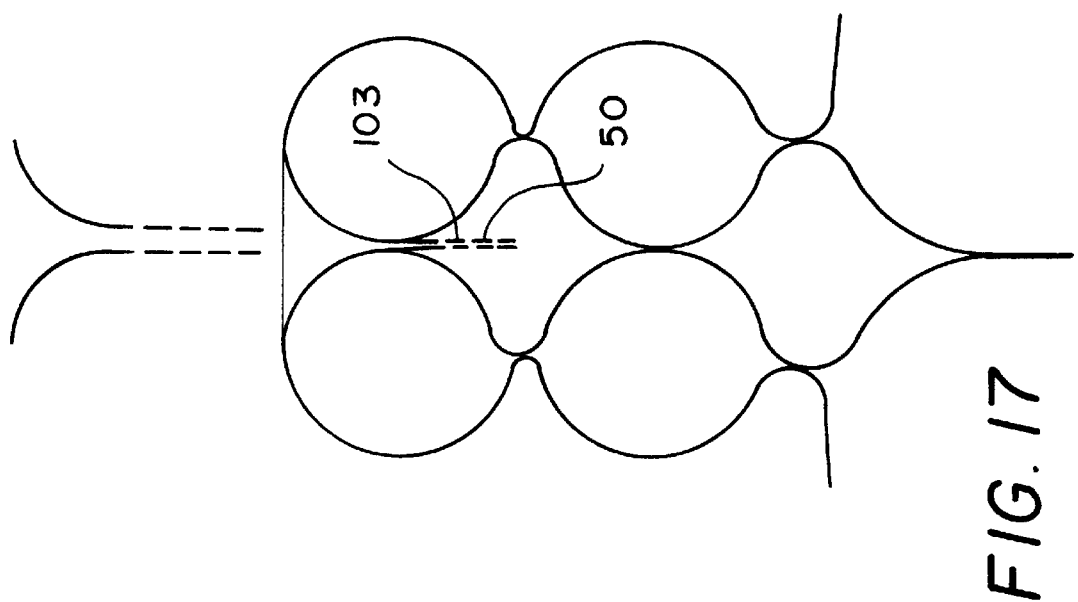

With reference to FIGS. 8 and 9, the access port consists, nominally, of an outer sleeve 30 and an inner sleeve 31. The applied pressure has the effect of inflating the outer sleeve 30 whilst collapsing the inner sleeve 31 causing the inner sleeve 31 to form a seal in the access passage to the abdominal cavity. This additional feature is intended to enhance the effectiveness of the seal, especially when the surgeon's arm has been removed from the sleeve.

The outer sleeve 30 is attached to the inner sleeve 31 at two diametrically opposed locations 32. This has the effect of locally constraining the outer sleeve effectively causing two "dimples" to form in the outer sleeve. The resulting force F acts on the inner sleeve causing the two walls of the inner sleeve to be held in contact. (This is similar in effect to inflating a balloon and stretching the neck of the balloon laterally instead of tying it off). Consequentially, the pressure of the gas in the abdominal cavity is required to overcome the pressure causing the inner sleeve to collapse plus the closing effect of the Force F in order for leakage to occur.

Referring now to FIGS. 10 to 27, a preferred embodiment of the access port will now be described. The access port of this third embodiment is based on and is a further development of the access port in the third embodiment. The access port in this embodiment is indicated generally by reference numeral 40. The access port 40 comprises an inner sleeve 41 and an outer sleeve 42. The outer sleeve 42 has a flange 44 provided at the distal end thereof.

Referring initially to FIGS. 10–12, the access port in the third embodiment, will be described. In use, the access port is adhesively attached to the exterior of a patient's abdominal wall, with or without an incise drape, so that the inner sleeve 41 projects into the abdominal cavity (See FIG. 10). As usual with minimally invasive surgery procedures, the patient's abdomen is inflated with gas at pressure P as shown in FIG. 11. The gas acts to expand the abdominal cavity. (Fluid pressure always acts perpendicular to the enclosing surfaces). Leakage of gas through the incision site causes gas to enter the chamber formed between the inner sleeve 41 and outer sleeve 42. Insulflation pressure can be introduced through a regulating valve (e.g. common stock-cock valve) attached to the outer sleeve 42.

The pressurised gas acts to inflate the outer sleeve 42 whilst, simultaneously, causing the opposing sides of the inner sleeve 41 to be forced into mutual contact. As shown in FIG. 11, this results in the formation of a chamber 46 formed between the inner sleeve 41 and the outer sleeve 42 when inflated. This effectively seals the abdominal cavity from atmospheric pressure which exists outside the abdomen. The force keeping the inner sleeve sealed is directly proportional to the pressure within the abdomen so the greater the gas pressure, the greater the force acting to create the seal.

As shown in FIG. 11, when the device is inflated, the outer sleeve 42 nominally forms a cylinder. The diameter D of the cylinder is determined by the circumference C of the outer sleeve 42. The inner sleeve 41 is connected to diametrically opposite points on the outer sleeve 42. The nominal diameter of the inner sleeve 41 is smaller than that of the outer sleeve 42, so the outer sleeve 42 is pulled towards the inner sleeve 41 to obtain the same diameter D when assembled. When insulflation pressure is introduced into the outer chamber, the outer chamber will form a nominal cylinder of diameter D which will hold the inner sleeve 41 taut in the transverse plane.

Although, insulflation pressure is contained with the construction shown in FIG. 11, difficulty is experienced in inserting a hand and arm through the access passage since the inner sleeve 41 would cling to the surgeon's hand and arm. The surgeon must work his hand forward through the access passage against the action of the insulflation pressure acting on the inner sleeve 41. This problem is overcome by the embodiment shown in FIGS. 13 and 14 in which the inner sleeve 41 is welded locally to the outer sleeve 42 along the weld lines 45 indicated in FIG. 20. The effect of the weld line 45 is that, when inflated, the outer sleeve 42 pulls the inner sleeve 41 outward as shown in FIG. 14. Since the weld line 45 does not extend the full width of either of the inner sleeve 41 or outer sleeve 42, gas can leak past the weld line as shown in FIG. 13 thereby inflating the chamber between the inner sleeve and outer sleeve resulting in the formation of upper sub-chamber 48 and lower sub-chamber 47. Since the upper sub-chamber 48 is subjected to insulflation pressure, the walls of the upper portion of the access passage are still held in mutual contact, forming a seal 100. Ideally the distance between this upper seal 100 and the distal end of the inner sleeve 41 should be greater than the distance between the surgeon's wrist and finger tips thus ensuring that, with his arm inserted, the device forms a seal with his wrist before his fingers exit the distal end of the inner sleeve 41.

Figure 15:
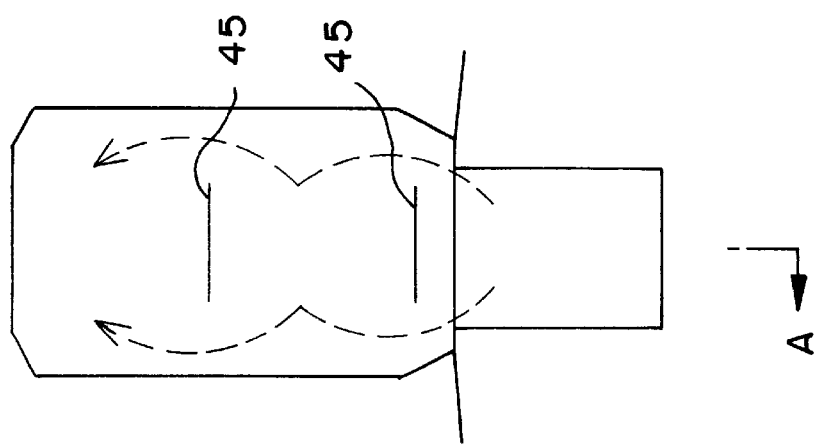
FIG. 15 is a schematic diagram of the access port of the invention showing the inclusion of two weld lines.

Ease of access through the access port is enhanced by including further welded connections 45,45' between the inner sleeve and the outer sleeve 42 as shown in FIG. 15. The inclusion of weld line 45' forms another line of seal indicated by reference numeral 101 on FIG. 15. This seal results in the formation of upper sub-chamber 48' and lower sub-chamber 47' between the inner sleeve 41 and the outer sleeve 42 and further increases the rigidity of the device thereby enhancing ease of access for the surgeon's hand.

The effectiveness of the upper seal 100 is further enhanced by the provisions of a flap valve 50 having a feathered edge construction (see FIGS. 17–24). The feathered edges are achieved by having the bottom end of the valve diameter larger than the inner diameter D so that the feathered edges have to be forced inwards to achieve the same diameter D. The edges allow the gas to pass between the flap valve 50 and the inner sleeve 41 and enables the valve to operate in the desired way and to conform around the surgeon's arm. The feathered edge is only required to extend downward from the line of the upper seal 100. The attachment of the flap valve 50 to the inner sleeve 41 is at positions A and B shown in FIG. 18. This prevents the flap valve 50 from attaching to the inner sleeve which results in greater flexibility and hence conformity of the flap valve 50 to the surgeon's arm. Finally, in the event that any gas leaks through this combination of seals, the outer sleeve 42 is tapered so that a final seal can be produced between the lip edge of the mouth of the device and the surgeon's forearm.

Figure 16:
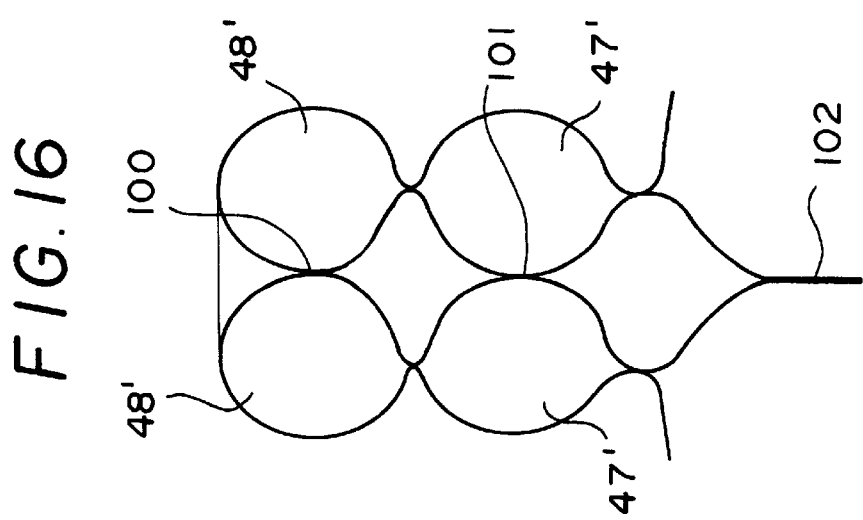
FIG. 16 is a sectional view along the line A—A of FIG. 15.
Figure 21:
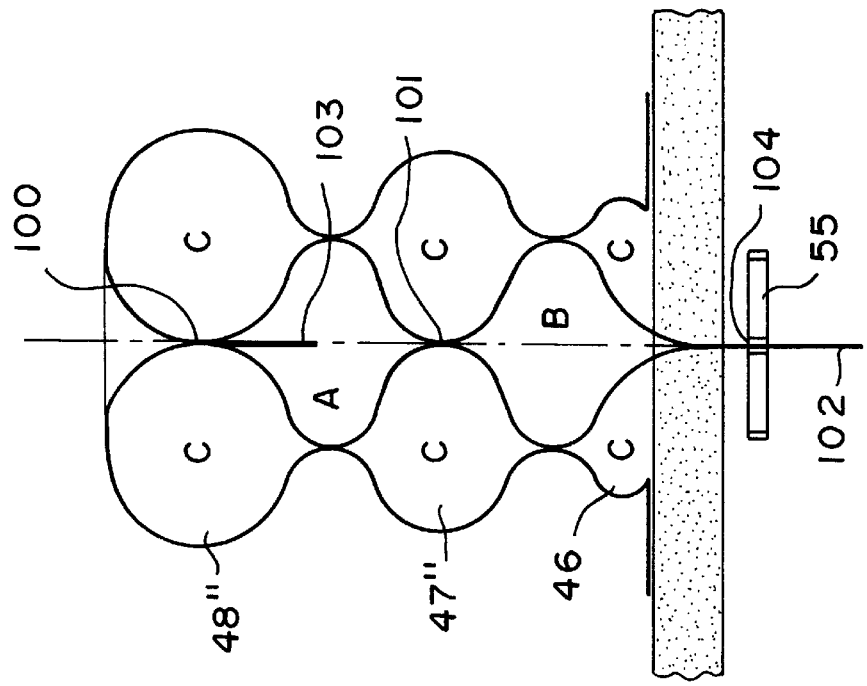
FIG. 21 is a sectional view along the line A—A of FIG. 20.
Figure 20:
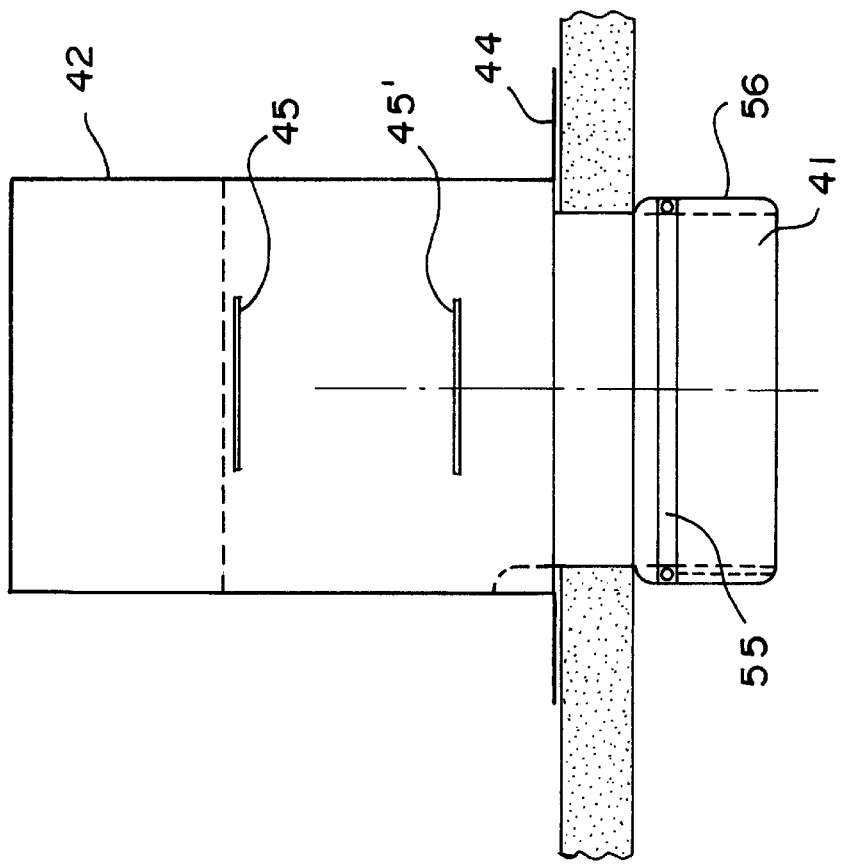
FIG. 20 is a front view of the third embodiment of the access port of the invention.

As indicated on FIG. 11, the gas pressure necessary to keep the inner sleeve sealed tends to act in such a way that the access port would experience a force F which would cause the inner sleeve 41 to turn inside out. To overcome this tendency the inner sleeve 40 and outer sleeve 42 are welded together along the line of their seams as shown in FIGS. 15 and 16. This overcomes the problem of the tendency to invert in respect of the proximal end of the inner sleeve 41. However, the distal end of inner sleeve 41 which projects into the abdominal cavity may still demonstrate a tendency to turn inside out.

The tendency for the distal end of the inner sleeve 41 to invert under the action of the insulflation pressure is overcome by the inclusion of a resilient arcuate tensioning device comprising arcuate bands 55 as shown in FIGS. 14, 15, 16 and 18. The inner sleeve is modified by the addition of two wings 56. The material forming the inner sleeve is cut to include the wing like projections as indicated. The edges of the inner sleeve are welded as previously described. The wings 56 are welded together with short linear welds. This has the effect of making the wings 56 stiff. These wings 56 provide an anchoring area for the tensioning device. The two arcuate bands 55 are welded together, through the wings 56, forming intimate joints. The arcuate bands 55, being compressed during assembly as indicated, apply a lateral pull to the inner sleeve 41 bringing the opposing faces of the inner sleeve 41 104 into mutual contact and hence forming an initial seal without the action of insulflation pressure. The eventual application of insulflation pressure results in the formation of further seals as described above. The geometry of the arcuate bands 55 is such that, when presented at right angles to the incision, it is possible for them to pass through the incision. Once in position within the abdomen, the bands 55 align themselves nominally parallel to the abdominal wall. In this attitude the insulflation pressure acts to invert the inner sleeve 41 but since the arcuate bands 55 cannot pass through the incision, the inner sleeve 41 is restrained. Finally, the stiffness resulting from the short linear welds in the wings 56 combined with the fact that the arcuate bands are welded to the wings 56 keeps the wings 56 nominally perpendicular to the arcuate bands preventing inversion of the extreme distal end of the inner sleeve.

The use of the device in the third embodiment will now be described.

With or without an incise drape having been applied, a suitable incision is made in the patient's abdominal wall penetrating the peritoneum. The distal end of the access port 40 is presented to the incision site and the tensioning device is pressed through to the peritoneal cavity. The adhesive connection is made between the flange 44 and the patient's skin, or incise drape if the latter is being used. Obviously, all parts of the access port 40 are subject to atmospheric pressure at this stage. Assuming a gas delivery port is in situ, insulflation pressure is applied to the patient's abdominal cavity. The action of the arcuate band on the inner sleeve in providing a lateral pull, effectively seals the inner sleeve. As the insulflation gas is introduced, leakage occurs at the incision site causing sub-chambers 48", 47", 46 to fill with gas (see FIGS. 20 and 21). The device inflates as previously described and the inner sleeve forms the upper seal 100 and middle seal 101. The action of the gas on the distal end of the inner sleeve 41 further enhances the lower seal 102. Since the pressure in cavity A is at atmospheric pressure, the flap valve 50 is not acting.

The surgeon then introduces his hand through the upper seal 100 and the middle seal 101. His hand passes through the incision and towards the lower seal 102. At this point his wrist is in the upper seal 100. Further movement forward causes the lower seal 102 to open. Gas leaks past the surgeon's fingers and enters cavities B and A. The flap valve 50 is now subject to a pressure differential with atmospheric pressure on one side and insulflation pressure on the other. This causes the feathered edge of the flap valve 50 to conform to the surgeon's forearm thus ensuring a seal 103. The lower seal 102 is now inactive. The surgeon can now move his hand further into the abdominal cavity, usually until his hand has exited the distal end of the inner sleeve. The gas seal is still maintained at the upper seal 100. In the event that, through excessive movement of the surgeon's arm, gas should escape past the upper seal 100 the pressure in cavity A will drop below insulflation pressure. If further leakage occurs at the middle seal 101 the pressure in cavity B will also drop below insulflation pressure. If this happens, a pressure differential exists across the lower seal which will become active causing the inner sleeve to conform to the surgeons arm at the distal end of the inner sleeve thus effecting a seal there. If, by chance, the lower seal is opened due to further excessive movement then gas will leak, ultimately, into cavity A causing the upper seal to activate. Thus, it is clear that the device is configured so that the failure of one seal automatically initiates the activation of the other.

Assuming that the upper seal 100 is active, removal of the surgeon's hand occurs as follows. Retraction of the arm until the wrist is in the upper seal 100 will cause no effect except that the arcuate band will cause the lower seal 102 to be held closed by its spring action. Once the hand has entered the upper seal 100, a leak path will be formed allowing gas to escape to atmosphere. Instantaneously, the pressure in cavities A and B will fall causing, once again, a pressure differential to exist across the lower seal which will become fully active. In the event that the lower seal 102 were the active seal at the commencement of the withdrawal, the passage of the hand through this seal would cause a leak path here causing the upper seal 100 to immediately become active.

With the surgeon's arm withdrawn, the distal end of the inner sleeve 41 will attempt to invert. However inversion is prevented by the fact that the arcuate bands 55 cannot pass through the incision in the orientation shown. As previously explained, the stiffness of the wings 56 on the inner sleeve 41 further act to prevent inversion. In the unlikely event that inversion does occur, the resulting leakage would cause the upper seal to automatically activate.

Removal of the device after surgery is relatively straightforward. After insulflation pressure has been removed, and with the device flaccid, the adhesive band at the flange is broken. This permits the arcuate band to be reoriented to present its narrow edge to the incision. A gentle pull on the welded seam of the inner sleeve 41 will cause the end of the arcuate band 55 to exit the incision, where it can be gripped firmly and withdrawn.

The access port essentially consists of a flexible tube, fabricated from polymer film edge welded, and an adhesive coated flange also of flexible polymer film. The tube is partially inverted as shown in FIG. 10(i) such that the end of the tube which is not attached to the flange projects beyond the flange. This configuration effectively forms the inner and the outer sleeves as described. For ease of manufacture, the two walls of the inner sleeve are made separate from the outer sleeves and welded to the outer sleeve, together with the material forming the feathered edge of the flap valve 50, along the lip edge. The flap valve 50 is manufactured by welding the two further pieces of polymer film which makes up the flap valve 50 inside the inner sleeve.

With reference to FIG. 29, a fourth embodiment 110 of the access port device is shown, which is a two part construction, a lower portion 115 and an upper portion 120. Both portions 115, 120 have a flange 125 which can be joined together by an adhesive or other mechanism. The lower portion 115 is provided with a leak path 130 which can be opened after the portions 115 and 120 are joined by removing a peel tab (over the leak path). In all other respects the device is similar to the third embodiment of access port device already described.

Referring to FIGS. 30 and 31 of the drawings, the surgical instrument of the second aspect of the present invention is indicated generally by reference numeral 201 and includes a handle 202 provided with a trigger 203 which is pivotally connected to the handle 202. The instrument 202 also includes an elongate shaft 204 and a detachable instrumentation head 205. The shaft 204 and instrumentation head are detachably connectable together by attachment means 206. As shown in the drawings, the instrumentation head 205 is provided with a stapling device. Obviously, any particular alternative surgical instrument such as a forceps, for instance, may be provided on the instrumentation head 205.

In use, the shaft 204 of the surgical instrument 201 is inserted into the valve (not shown) on the trocar sleeve which is indicated generally by reference numeral 210. The shaft 204 is pushed through the barrel 211 of the trocar sleeve 210 which is of approximately from 3 mm to 6 mm internal diameter. In the prior art, the internal diameter of the trocar barrel and the shaft 204 is typically up to 15 mm in diameter so as to accommodate an instrument head of that size.

In use, the detachable instrumentation head 205 is held in the hand of the surgeon and the appropriate instrumentation head 205 provided with the required instrument is connected to the shaft 204 by the attachment means 206. The trigger 203 is operated by the surgeon so as to control and manipulate the stapling device provided on the detachable instrumentation head 205.

It is to be understood that the attachment means 206 is variable as are the dimensions of the instrumentation head 205 since the latter is not restricted by the dimensions of the trocar sleeve 211.

Reference is now made to the surgical incise drape device of the invention.

There are four general ways in which the incise drape can be used:

1. The invention may be used as a means of attachment of a device such as an access device or access port for use in minimally invasive surgery such as described above on which is applied a significant force from the gas pressure that is applied once pneumoperitoneum is established; or forces arising from the manipulation of those access ports from the hand or instruments.

2. It may be used as a means of attachment to make current devices such as the numerous cannula used in minimally invasive surgery leak free—in this instance the device can be made to fit over the current cannula with an adhesive flange that will stick to the drape. It would also serve the purpose of fixing those devices in place so that they do not slide through the trocar wound and be used when a surgeon desires to put into place a smaller cannula that the wound would allow.

3. Furthermore, the invention can be used as a means to apply an external pulling force on the patients skin and attached tissue (subcutaneous tissue, muscle, Peritoneum) for many purposes. One such purpose would be a gasless means to lift the abdominal wall to create a cavity similar to that created by pneumoperitoneum, or the gasless "laprolift" that uses an internal device to lift the abdominal wall for a gasless procedure. Another purpose would be lifting the abdominal cavity to allow the "first trocar" incision to make it safer. Also it could be used as a tissue retractor, by pulling from the attachment point(s) of the drape on both sides of a surgical would, etc.

4. The incise drape could be also used in a situation with a combination of gas and pull requiring less gas pressure. Similar to 3 above, a means of pulling on the attachment point(s) is used to reduce the amount of gas pressure required to make a cavity for the purpose of the minimally invasive surgery procedures. By way of example if one was to pull on the hand access port included in our previous patent application, less gas pressure would be required to fill the body cavity to produce the same space that is made from pressure alone. As gas pressure has some severe complications in selected patients, and is often difficult to work with, this technique could be a significant advantage in minimally invasive surgery, for instance.

It will of course be understood that the invention is not limited to the specific details described herein, which are given by way of example only, and that various modifications and alterations are possible within the scope of the invention as defined in the appended claims.

I claim:

1. An access port for use in surgery comprising:

an elongate sleeve of flexible material having an entry opening located at a proximal end of the sleeve and an exit opening located at a distal end of said sleeve, an inflatable chamber surrounding said sleeve and extending substantially coaxially therewith from the proximal end of the sleeve for a distance along the length of said sleeve, said inflatable chamber when inflated operating to collapse said sleeve to close said entry opening, said sleeve being attached to and surrounded by said inflatable chamber with said sleeve extending through said inflatable chamber and outwardly therefrom to provide a projecting flexible sleeve portion extending outwardly from the inflatable chamber to the exit opening at the distal end of said sleeve whereby said projecting sleeve portion can be inserted through an incision and into a patient's body cavity to provide a flexible sleeve portion adjacent to said exit opening within said body cavity free of a surrounding inflatable chamber.

2. An access port according to claim 1, wherein the inflatable chamber is of generally "hour-glass" profile defining an upper chamber and a lower chamber, the lower chamber being insertable into the incision made in the patient's body cavity.

3. The access port of claim 2 wherein a laterally extending flange is secured to said upper chamber in spaced relationship to said lower chamber to affix the access port externally to a patient.

4. An access port as claimed in claim 1 wherein said sleeve is formed with two opposed, substantially flat sleeve sidewalls which collapse together into contact in response to pressure in said inflatable chamber.

5. An access port as claimed in claim 4 wherein said entry opening and access opening are elongate openings defined by the sleeve sidewalls of said sleeve.

6. The access port of claim 5 wherein the sleeve sidewalls of said sleeve are formed to provide a flap valve at said exit opening.

7. The access port of claim 6 wherein a flange is secured to said inflatable chamber in spaced relationship to the proximal end of said sleeve, for affixing the access port externally to a patient, said flange extending laterally relative to said projecting sleeve portion.

8. The access port of claim 4 wherein said sleeve forms an inner wall for said inflatable chamber, said inflatable chamber having a chamber outer wall including two flat chamber sidewalls coextensive with said sleeve sidewalls.

9. The access port of claim 8 wherein said sleeve sidewalls and chamber sidewalls are sheets of gas impermeable flexible material bonded at their common side edges and proximal ends.

10. The access port of claim 8 wherein the sleeve sidewalls of said sleeve are formed to provide a flap valve at said exit opening.

11. The access port of claim 10 wherein at least a first flap valve is formed within said sleeve to close said sleeve, said first flap valve being positioned in spaced relationship to the proximal and distal ends of said sleeve.

12. The access port of claim 11 wherein opposite sides of said sleeve are connected to the chamber outer wall at a location spaced from said sleeve proximal end so as to divide the inflatable chamber into upper and lower subchambers in fluid communication.

13. The access port of claim 12 wherein a flange is secured to said inflatable chamber in spaced relationship to the proximal end of said sleeve, for affixing the access port externally to a patient, said flange extending laterally relative to said projecting sleeve portion.

14. An access port as claimed in claim 13 wherein the sleeve sidewalls of said sleeve are formed to be wider adjacent to said exit opening to provide a wider section of said sleeve on said projecting flexible sleeve portion.

15. The access port of claim 14 wherein resilient tensioning units are secured to the projecting sleeve portion of said sleeve to force said sleeve sidewalls into contact at said exit opening.

16. An access port as claimed in claim 12 in which a separate tensioning device is provided in the distal region of the sleeve spaced from the distal edge to place the sleeve sidewalls under a generally transverse tension thereby creating a taut region across the sleeve operable as a further seal as part of an exit sealing means.

17. An access port as claimed in claim 16 in which the tensioning device comprises a pair of opposed arcuate bands operable to prevent retraction of the sleeve from the abdominal cavity.

18. An access port as claimed in claim 17 in which laterally projecting wings are provided at the side edges of the sleeve to provide anchoring points for the opposed arcuate bands.

19. An access port as claimed in claim 4 wherein the sleeve sidewalls of said sleeve are formed to be wider adjacent to said exit opening to provide a wider section of said sleeve on said projecting flexible sleeve portion.

20. The access port of claim 4 wherein the sleeve sidewalls of said sleeve are formed to provide a flap valve at said exit opening.

21. The access port of claim 20 wherein resilient tensioning units are secured to the projecting sleeve portion of said sleeve to force said sleeve sidewalls into contact at said exit opening.

22. The access port of claim 1 wherein a flange is secured to said inflatable chamber in spaced relationship to the proximal end of said sleeve, for affixing the access port externally to a patient, said flange extending laterally relative to said projecting sleeve portion.

23. The access port of claim 22 wherein said flange extends around but is spaced from said sleeve, said flange being oval in configuration.

24. The access port of claim 1 wherein said inflatable chamber includes chamber walls forming an enclosed inflatable chamber that in use is not in fluid communication with a patient's body cavity whereby the pressure in the inflatable chamber may be different from the pressure in the patient's body cavity, a pressure inlet being mounted on a chamber wall of said inflatable chamber.

25. The access port of claim 1 wherein said inflatable chamber extends to a lowermost chamber end which surrounds and is spaced from said sleeve, the projecting flexible sleeve portion extending outwardly from said lowermost chamber end, and a laterally extending flange is secured to said lowermost chamber end for affixing the access port externally to a patient, said flange being spaced from said sleeve.

26. The access port of claim 1 wherein at least a first flap valve is formed within said sleeve to close said sleeve, said first flap valve being positioned in spaced relationship to the proximal and distal ends of said sleeve.

27. The access port of claim 26 wherein said sleeve is formed with two opposed substantially flat sidewalls, the sidewalls of said sleeve being formed to provide a second flap valve at said exit opening.

28. The access port of claim 27 wherein said first flap valve is positioned in spaced relationship between said entry opening and said projecting flexible sleeve portion.

29. The access port of claim 28 wherein said first flap valve is formed of first and second sheets of flexible material each having a tethered end and a free end, the tethered end of said first sheet being connected to one of said sleeve sidewalls and the tethered end of said second sheet being connected to the remaining sleeve sidewall, the free ends of said sheets engaging to close said sleeve at a point spaced from said tethered ends in the direction of the distal end of said sleeve.

30. The access port of claim 1 wherein said inflatable chamber includes chamber walls forming an enclosed inflatable chamber that in use is not in fluid communication with a patient's body cavity whereby the pressure in the inflatable chamber may be different from the pressure in the patient's body cavity, a pressure inlet being mounted on a chamber wall of said enclosed inflatable chamber.

31. The access port of claim 30 wherein at least a first flap valve is formed within said sleeve to close said sleeve, said first flap valve being positioned in spaced relationship to the proximal and distal ends of said sleeve.

32. The access port of claim 1 wherein said sleeve forms an inner wall for said inflatable chamber, said inflatable chamber having a chamber outer wall spaced from said sleeve and connected to said sleeve at the proximal end of said sleeve.

33. The access port of claim 32 wherein opposite sides of said sleeve are connected to the chamber outer wall at a location spaced from said sleeve proximal end so as to divide the inflatable chamber into upper and lower subchambers in fluid communication.

34. The access port of claim 33 wherein the opposite sides of the sleeve are connected to the chamber outer wall at a plurality of opposite spaced locations.

35. An access port for use in surgery comprising:

an inflatable chamber having two, flexible, opposed substantially flat chamber inner sidewalls which collapse together into contact in response to pressure in said inflatable chamber, said inner chamber sidewalls defining a passage through said inflatable chamber between a chamber entry opening and a chamber exit opening at a chamber exit end;

and a flexible non-inflatable extension section secured to the chamber exit end of said inflatable chamber in communication with the passage therethrough, said extension section being adapted to be inserted through an incision into a patient's body cavity to provide a flexible sleeve portion extending outwardly from the inflatable chamber, said extension section having a sleeve entry opening and a sleeve exit opening and two substantially flat, flexible sidewalls which form a flap valve at said sleeve exit opening.

36. An access port as claimed by claim 35 wherein the inner chamber sidewalls form a second flap valve at said chamber exit.

37. An access port as claimed by claim 36 wherein a laterally projecting chamber flange is connected to said inflatable chamber to surround said chamber exit opening and a laterally projecting extension section flange is secured to said extension section to surround said sleeve entry opening, said chamber and extension flanges being secured together.

38. An access port device for use in surgery comprising a sleeve having an entry opening located at a proximal end of the sleeve and having an exit opening located at a distal end thereof for insertion into an incision made in a patient's body, the exit opening allowing access to the patient's body cavity, characterized in that the device includes exit opening sealing means provided by the sleeve being collapsible on itself by gas pressure within the abdominal cavity of the patient at or adjacent the distal edges of the sleeve, the sleeve being formed by sheets of flexible, gas impermeable, sterilisable, biocompatible material having joined side edges which are collapsible together by gas pressure within the abdominal cavity of the patient at or adjacent, the distal end of the sleeve so as to provide a seal, whereby when the patient's body cavity is inflated by gas, the exit sealing means prevents substantial leakage of gas from the patient's body cavity through the sleeve while providing access for a surgeon's hand or surgical instrument.

39. An access port as claimed in claim 38 having entry sealing means for sealing the sleeve in a region adjacent to the entry opening, whereby when the patient's body cavity is inflated by gas, the entry sealing means assists in preventing substantial leakage of gas from the patient's body cavity while providing access for a surgeon's hand while sealing about a surgeon's arm which extends outside the access port device.

40. An access port as claimed in claim 39, wherein the entry sealing means comprises an inflatable chamber arranged in surrounding relation to the sleeve and capable of exerting a pressure on the sleeve causing at least a portion of it to contract thereby sealing the entry opening.

41. An access port as claimed in claim 40 in which a separate tensioning device is provided adjacent to the distal end of the sleeve spaced from the exit opening to place the sheets forming the sleeve under a generally transverse tension thereby creating a taut region across the sleeve operable as a further seal as part of the exit sealing means.

42. An access port as claimed in claim 41 in which the tensioning device comprises a pair of opposed arcuate bands operable to prevent retraction of the sleeve from the abdominal cavity.

43. An access port as claimed in claim 42 in which laterally extending wings are provided at the side edges of the sleeve to provide anchoring points for the opposed arcuate bands.

* * * * *